(12) United States Patent
Murugkar et al.

(10) Patent No.: US 7,542,137 B2
(45) Date of Patent: Jun. 2, 2009

(54) PATHOGEN DETECTION USING COHERENT ANTI-STOKES RAMAN SCATTERING MICROSCOPY

(75) Inventors: Sangeeta Murugkar, Ottawa (CA); Hanan Anis, Kanata (CA); Xiaoliang Sunney Xie, Lexington, MA (US); Conor Evans, Boston, MA (US)

(73) Assignees: University of Ottawa, Ontario (CA); President and Fellows of Harvard College, Cambridge, MA (US)

( * ) Notice: Subject to any disclaimer, the term of this patent is extended or adjusted under 35 U.S.C. 154(b) by 77 days.

(21) Appl. No.: 11/781,602

(22) Filed: Jul. 23, 2007

(65) Prior Publication Data

US 2008/0059135 A1    Mar. 6, 2008

Related U.S. Application Data

(60) Provisional application No. 60/832,617, filed on Jul. 24, 2006.

(51) Int. Cl.
*G01J 3/44* (2006.01)
*G01N 21/65* (2006.01)

(52) U.S. Cl. .................................. 356/301; 356/36
(58) Field of Classification Search ............. 356/301
See application file for complete search history.

(56) References Cited

U.S. PATENT DOCUMENTS 6,950,184 B2 * 9/2005 Stewart et al. ............ 356/301

OTHER PUBLICATIONS

Grow et al, New Biochip Technology for Label-Free Detection of Pathogens and Their Toxins, Journal of Microbiological Methods, vol. 53, Issue 2, May 2003, pp. 221-233.*
"Broadly tunable dual-wavelength light source for coherent anti-stokes raman scattering microscopy", Ganikhanav et al, Optics Letters, vol. 31, No. 9, May 1, 2006.
"Optimization of coherent anti-stokes raman scattering microscopy using photonic crystal fiber", Murugkar et al (to be published in Proceedings of SPIE 2007).
"A fast method for detecting Cryptosporidium parvum oocysts in real world samples", Stewart et al, Advanced Biomedical and Clinical Diagnostic Systems III, SPIE, vol. 5692 (SPIE Bellingham, WA, 2005).
"Multi-focus coherent anti-stokes raman scattering microscopy", Hashimoto et al, Microsc. Microanal 9 (Suppl 2), 2003, Copyright 2003 Microscopy Society of America.

* cited by examiner

*Primary Examiner*—F. L Evans
(74) *Attorney, Agent, or Firm*—Allen, Dyer, Doppelt, Milbrath & Gilchrist, P.A.

(57) ABSTRACT

The invention provides a system and method for automatic real-time monitoring for the presence of a pathogen in water using coherent anti-stokes Raman scattering (CARS) microscopy. Water sample trapped in a trapping medium is provided to a CARS imager. CARS images are provided to a processor for automatic analyzing for the presence of image artifacts having pre-determined features characteristic to the pathogen. If a match is found, a CARS spectrum is taken and compared to a stored library of reference pathogen-specific spectra for pathogen identification. The system enables automatic pathogen detection in flowing water in real time.

24 Claims, 11 Drawing Sheets

Figure 1. Average spectrum plus standard deviations of A. cysts and B. river water

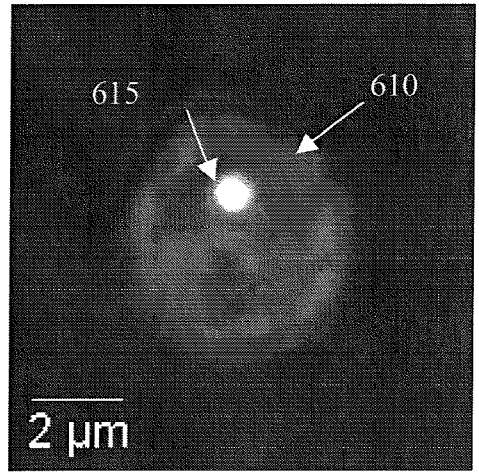
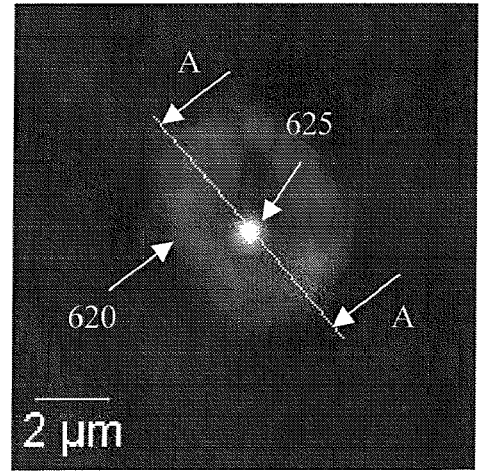
FIG. 6A　　　　　　　　　FIG. 6B
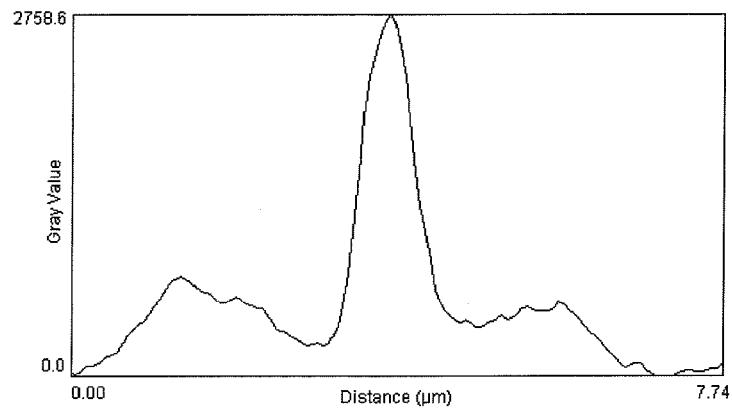
FIG. 6C

PATHOGEN DETECTION USING COHERENT ANTI-STOKES RAMAN SCATTERING MICROSCOPY

CROSS-REFERENCE TO RELATED APPLICATIONS

The present invention claims priority from U.S. Provisional Patent Application No. 60/832,617 filed Jul. 24, 2006, entitled "Pathogen Detection Using Coherent Anti-Stokes Raman Scattering (CARS) Microscopy", which is incorporated herein by reference.

TECHNICAL FIELD

The present invention relates generally to water contamination testing, and in particular to assessing occurrences of biological pathogens in aqueous samples using nonlinear microscopy.

BACKGROUND OF THE INVENTION

*Cryptosporidium parvum*, a protozoan microorganism, is one of principle contributors to water contamination and represents a major threat to human health. Ingestion of just a few oocysts can cause diarrhea and can be especially fatal in immuno-compromised individuals. There is no specific drug therapy proven to be effective to treat cryptosporidial infections. For these reasons, detection of *cryptosporidia* in water supplies is important. It is also important to be able to distinguish viable and non-viable *cryptosporidia* and infectious and non-infectious *cryptosporidia*.

*Cryptosporidia* occur outside the body of an animal primarily in the form of oocysts, which are environmentally stable and resistant particles having a diameter that is typically in the range from about 3 to about 6 micrometers. The oocysts are known to remain viable for extended periods of time and are resistant to conventional water disinfection methods. Due to massive shedding of oocysts in the feces of infected animals or individuals and the robust nature of the oocysts, they are frequently present in raw surface water and even in finished drinking water. Each oocyst typically contains four sporozoites, each of which can independently infect a host upon ingestion by the host of the oocyst. Extended exposure to the environment, treatment with certain chemicals, exposure to ultraviolet radiation, and other unknown factors can render sporozoites within an oocyst non-viable, i.e., unable to infect a host upon ingestion of the oocyst.

Current methods used in the water quality testing industry for detection of *cryptosporidium* oocysts are time-consuming, labor intensive and require highly trained microscopists. These methods rely on microscopic examination of samples that are stained with fluorescent antibodies for the presence of *cryptosporidium* oocysts. The cross reaction of the antibodies with targets in the sample other than the specific pathogen, often gives false positive results. In the particular case of parasitic protozoa such as *cryptosporidium* and *giardia*, if the antibody only reacts with certain variants of the protozoa, but not with the variant present in the water sample being tested, the immunological test can fail to detect the pathogen even when it is present.

In contrast, vibrational spectroscopic techniques such as spontaneous Raman scattering provide specific molecular information on samples. Pathogens can be "fingerprinted" by means of characteristic vibrational frequencies of the molecular species, even in a complex multi-component mixture as disclosed for example in U.S. Pat. No. 6,950,184, which is incorporated herein by reference.

In Raman spectroscopy, incident light having frequency $\omega_p$ is absorbed by a sample and is re-radiated at a shifted frequency $\omega_s = \omega_p - \Omega$, where $\Omega$ corresponds to a transition between two vibrational states of molecules in the sample, also referred to as a vibration frequency. The difference between the frequencies of the incident and re-radiated light is known as the Raman shift (RS), and is typically measured in units of wavenumber (inverse length). If the incident light is substantially monochromatic (single wavelength) as it is when using a laser source, the scattered light which differs in frequency can be more easily distinguished by filtering.

As an example, FIG. 2, which is reproduced here from an article by S. Stewart et al, Proc. of SPIE, Vol. 5692, 341-350 (2005), illustrates a typical Raman spectrum of a *cryptosporidium* oocysts (A) in comparison with a Raman spectrum from river water (B). As seen from the figure, the spontaneous Raman spectrum (A) of *cryptosporidium* oocysts is dominated by the presence of a strong peak around Raman shift of 2930 cm$^{-1}$ corresponding to stretching vibrations of a C—H bond, which can be used as an indicator of the presence of *cryptosporidium* oocysts in water.

One disadvantage of using the aforedescribed spontaneous Raman scattering for water testing relates to low characteristic cross-sections of spontaneous Raman scattering, which resulting in low signal levels and hence considerable amount of time needed to record a Raman spectrum. Additionally, the application of conventional Raman spectroscopy can be disadvantageously affected by a background fluorescence signal, which often limits the sensitivity of detection. Furthermore, the Raman spectra analysis for the detection of *cryptosporidium* oocysts disclosed in the prior art U.S. Pat. No. 6,950,184 is not capable of discerning between individual organisms and how many oocysts are present in a sample, and is therefore not well suited for quantitative analysis of the oocysts concentration in water.

There is another optical analysis method based on probing vibrational energies of molecules in a sample, namely—a coherent anti-Stokes Raman scattering (CARS) microscopy. CARS is a third order nonlinear optical process and involves simultaneous excitation of a sample under test with two light beams—a pump laser beam at a frequency $\omega_p$ and a Stokes laser beam at a frequency $\omega_s$, resulting in a signal at the anti-Stokes frequency of $\omega_{as} = 2\omega_p - \omega_s$ being generated in a phase matching direction, provided that the frequency difference between the pump and Stokes beams corresponds to a transition between two vibration energy levels of sample molecules, i.e. $\Omega = \omega_p - \omega_s$; an energy diagram for this process is shown in FIG. 1. In CARS spectrography, the intensity of the signal at the anti-Stokes frequency $\omega_{as}$ is typically plotted as a function of the frequency shift $\Omega$ between the pump and Stokes signals and is referred to as the CARS spectrum, with the frequency shift $\Omega$ referred to as the anti-Stokes frequency shift or CARS frequency shift and is typically expressed in units of cm$^{-1}$. Although the CARS microscopy has been applied recently to imaging of live cells in laboratory conditions, see for example U.S. Pat. No. 6,108,081 issued to Holtom et al, it has been largely unknown in the water testing industry.

Therefore the water testing industry currently lacks a method that can provide a fast and reliable detection of waterborne pathogens such as *cryptosporidium* oocysts and can be used for real-time automated water testing.

An object of the present invention is to overcome the shortcomings of the prior art by providing a method for assessing the presence of individual pathogen organisms in a sample utilizing CARS microscopy for fast pathogen detection and identification.

Another object of the present invention is to provide a method for assessing the presence of individual pathogen organisms in a sample that can be used for automated water monitoring in real-time.

SUMMARY OF THE INVENTION

In accordance with the invention, there is provided a method of assessing the presence of a pathogen in a sample comprising the steps of: a) irradiating the sample with first radiation having a spectrum centered at a first frequency and second radiation having a spectrum including a second frequency, wherein the first frequency exceeds the second frequency by a pre-determined non-zero frequency shift characteristic to the pathogen; b) detecting third radiation scattered from or transmitted through the sample at a third frequency that is different from the first and second frequencies, so as to form an image of at least a portion of the sample; and, c) analyzing the image to assess occurrence of one or more image artifacts each having one or more pre-determined features characteristic of the pathogen.

The method may further comprise the step of obtaining a spectrum of the third radiation if the presence of an image artifact having one or more pre-determined features characteristic for the pathogen is detected in step (c), for performing pathogen identification by comparing the spectrum to one or more stored reference spectra characteristic to one or more pathogens.

According to one aspect of the invention, the third radiation results from a coherent anti-Stokes Raman scattering (CARS) of the first and second radiation within the pathogen, so that the third frequency exceeds the first frequency by an anti-Stokes frequency shift equal to the pre-determined non-zero frequency shift and corresponds to a molecular vibration frequency in the pathogen.

According to another aspect of the invention, the method further comprises the step of flowing water through a trap medium for accumulating the pathogen therein to form the sample, so as to continuously monitor the water for the presence of a pathogen.

Another aspect of the present invention provides a system for automatic real-time monitoring of the presence of a pathogen in water. The system comprises a trap medium, water directing means for directing the water through the trap medium for trapping the pathogen in the trap medium for forming a sample, means for moving the trap medium carrying the sample out of the water, a CARS optical source for generating a pump beam at a pump optical frequency and a Stokes beam at a Stokes optical frequency, a CARS imaging system for obtaining an image of the sample, and a processor programmed for analyzing the image to assess occurrence of one or more image artifacts having a shape, size or intensity pattern that is characteristic to the pathogen.

The CARS imaging system comprises optical means for directing the pump and Stokes beams coaxially onto a portion of the trap medium comprising the sample, and an optical detector for detecting light from the aqueous sample at a frequency that is shifted from the pump optical frequency by a CARS frequency shift for forming an image of a portion of the sample;

According to one aspect of the invention, the CARS imaging system further comprises a microlens array means for focusing the pump and Stokes beams into a plurality of focal locations in the sample, and a photodetector array for detecting optical radiation generated at each of the plurality of focal locations. In one embodiment, the spinning micro-lens array disk for raster scanning the sample for forming the image.

BRIEF DESCRIPTION OF THE DRAWINGS

The invention will be described in greater detail with reference to the accompanying drawings which represent preferred embodiments thereof and in which like reference labels are used to indicate like elements, wherein:

FIGS. 6A and 6B are two exemplary CARS images of live *cryptosporidium parvum* oocysts obtained using an embodiment of the CARS optical source shown in FIG. 4;

FIG. 6C is a plot showing intensity profile of the CARS image of the live *cryptosporidium parvum* oocysts corresponding to the image cross-section AA in FIG. 6B;

DETAILED DESCRIPTION

Figure 1:
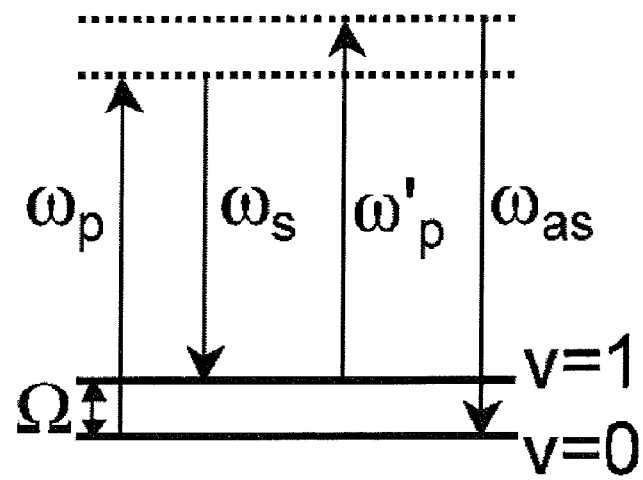
FIG. 1 is an energy diagram of a CARS process according to prior art.

The invention includes a method for detecting *Cryptosporidium parvum* organisms, in particular *Cryptosporidium* oocysts, and other waterborne pathogens using CARS imaging and/or spectroscopy in a variety of aqueous or non-aqueous samples, including but not limited to, environmental raw water samples, backwash water samples, process water samples, finished water samples, and samples carried by a pathogen trapping medium. The invention also includes a method and system for real time water monitoring for the presence of a particular pathogen such as the *Cryptosporidium parvum* in water reservoirs and flowing water.

Reference will now be made in detail to the embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to obscure aspects of the present invention unnecessarily.

One aspect of the invention relates to an application of CARS microscopy to detect occurrence of *cryptosporidium* oocysts from water samples, and can also be used to detect other pathogens in contaminated water. The present invention overcomes the shortcomings of prior art methods and enables speed, sensitivity and chemical selectivity in the detection of the oocysts, and enables automated real-time monitoring of water supply. In general, pathogens are micro-organisms that cause disease in humans. The term "pathogen" will be used herein to refer to a particular pathogen species, such as the *cryptosporidium parvum* or *Giardia*, while the terms "pathogen organism" or "individual pathogen" will be used to refer to individual pathogen organisms such as individual *cryptosporidium parvum* oocysts.

Each particular pathogen has it own distinct spectrum of vibration frequencies. By tuning the difference between the pump and the Stokes beams frequency, i.e. the CARS frequency shift in a frequency range containing the molecular vibration frequencies of a particular pathogen, a CARS spectrum is obtained. This spectrum is hence characteristic to the particular pathogen.

In general, the molecular vibration frequencies of most pathogens occur in the range of 500-3250 $cm^{-1}$ giving rise to peaks in the CARS spectrum at the respective frequencies. The residual body consisting of the lipid vacuole inside the *cryptosporidium* oocyst has large concentrations of C—H vibration bonds with characteristic frequencies in the range of 2810-2870 $cm^{-1}$, giving rise to a strong CARS signal that is used in the invention for imaging the oocysts in a water sample. Other peaks in the CARS spectrum such as those due to amide vibrations that occur in the range of 1650+\−25 $cm^{-1}$, can also be used for imaging the oocysts as well as to distinguish between various pathogens.

Figure 2:
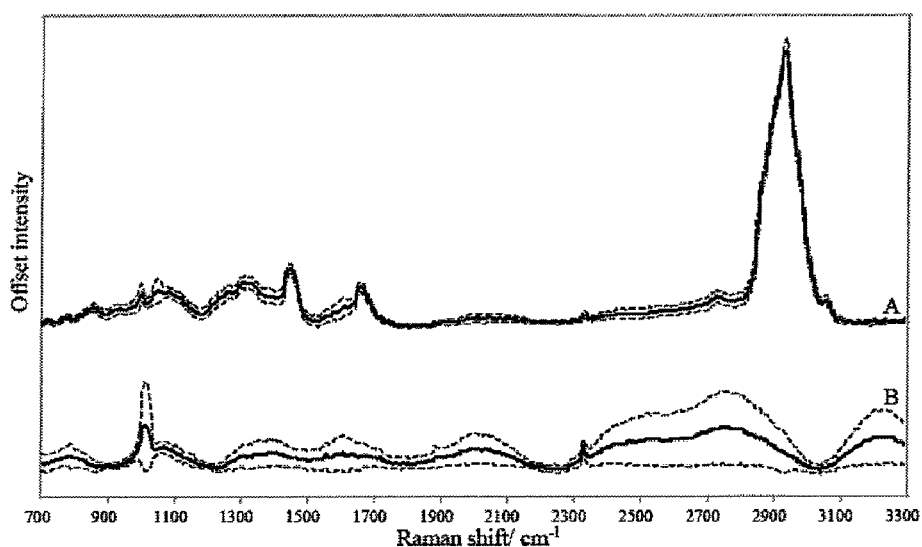
FIG. 2 is a prior art plot showing Raman spectra of *cryptosporidium parvum* oocysts.

A specific example of an application of the CARS microscopy to detect the presence of *cryptosporidium* oocysts is described herein below. As shown in FIG. 2, a spontaneous Raman spectrum of *cryptosporidium* oocysts is dominated by the presence of a strong peak around Raman shift of 2930 $cm^{-1}$ corresponding to the C—H stretching vibrations in this particular pathogen. In the CARS spectrum a corresponding peak occurs at around 2840 $cm^{-1}$; the ~90 $cm^{-1}$ difference between the Raman shift and the CARS shift includes contribution from non-resonant CARS background signal stemming from optical nonlinearities in the pathogen excitation process unrelated to the C—H bond vibrations.

In one embodiment of the present invention the frequency difference between the pump and anti-Stokes beams is tuned to this CARS frequency of 2840 $cm^{-1}$+\−60 $cm^{-1}$, preferably +\−25 $cm^{-1}$, and most preferably +\−10 $cm^{-1}$, which corresponds to a peak in the CARS spectrum associated with the C—H vibrations in *cryptosporidium* oocysts. Alternatively, the frequency difference between the pump and anti-Stokes beams is tuned to 1650+\−25 $cm^{-1}$, or preferably to 1650+\−10 $cm^{-1}$. Alternatively, the frequency difference between the pump and anti-Stokes beams is tuned to 2950+\−50 $cm^{-1}$, or preferably to 2950+\−10 $cm^{-1}$. The pump and Stokes beams overlapped in a small focal volume, preferably less than 1 $\mu m^3$, within the sample, are scanned across the sample in a same focal plane. In this manner, CARS images of a scanned portion of the sample are obtained, for example in forward and/or epi-direction of detection, where the epi-direction is the direction of back-scattering and is opposite to the forward direction.

Figure 3:
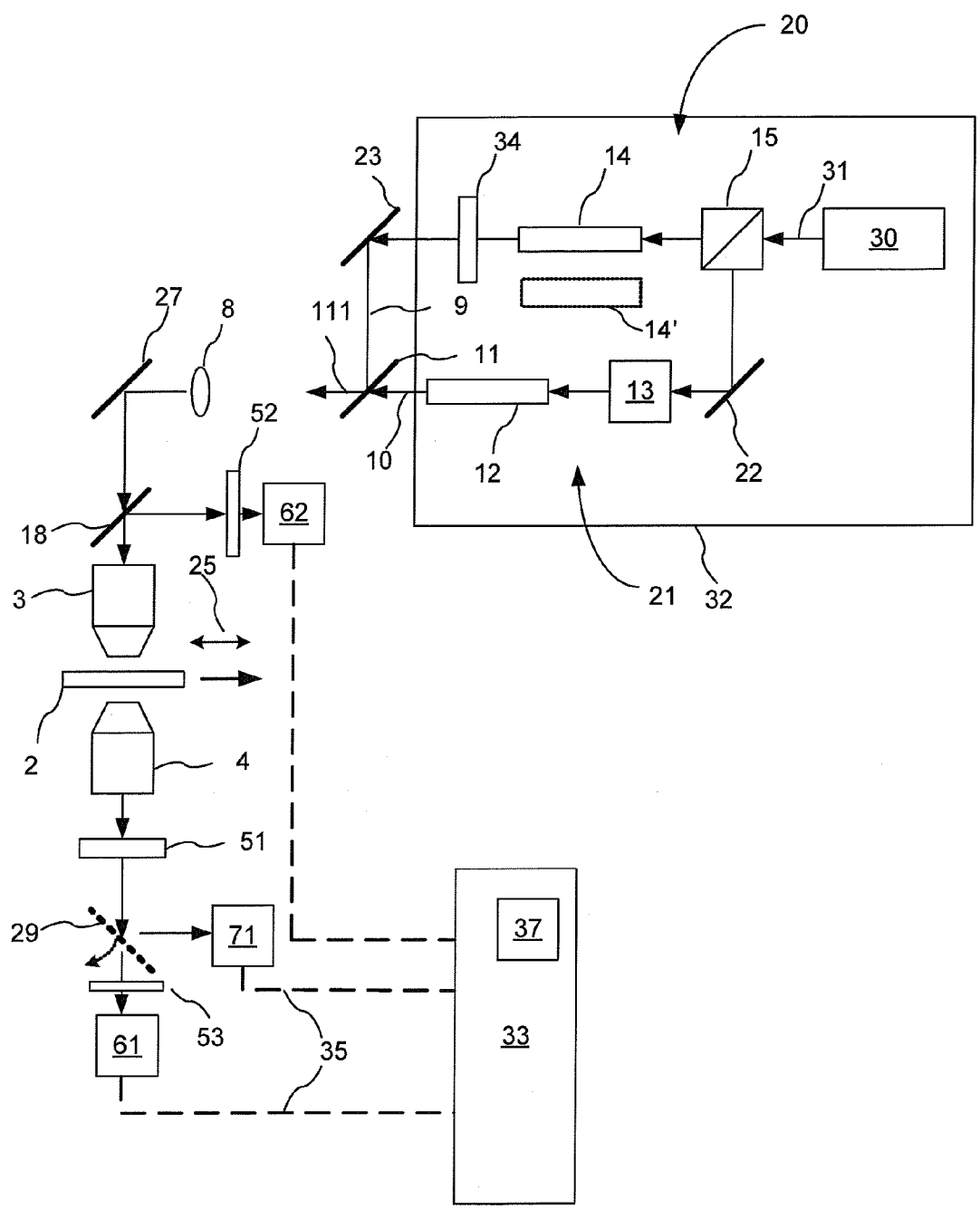
FIG. 3 is a schematic block diagram of a CARS apparatus for detecting the presence of a pathogen in a sample according to the present invention.

An exemplary embodiment of an apparatus for detecting the presence of a pathogen in a sample using the CARS technique in accordance with the present invention is illustrated in FIG. 3 and will now be described.

In this particular implementation of the CARS technique, a single femtosecond optical source is used to obtain both the pump and Stokes beams, which significantly simplifies the apparatus and reduces its cost. Advantageously, the apparatus of FIG. 3 enables image and spectrum acquisition from a same single CARS signal without the need to tune the wavelength of the optical source, and provides good quality images wherein characteristic features of a particular pathogen are easily discernable. The apparatus of FIG. 3 utilizes an improvement to the conventional CARS known as multiplexed CARS spectroscopy, wherein spectral width of the Stokes pulse determines a range of molecular vibrational energies that are probed, while the spectral width of the pump pulse determines the spectral resolution of the technique. In order to achieve a high spectral resolution, the pump pulses have to be spectrally narrow and the Stokes pulses have to be spectrally broad. To achieve a spectrally broad Stokes pulse, one embodiment of the apparatus may utilize a photonic crystal fiber (PCF) having suitable chromatic dispersion and nonlinear characteristics so as to generate a so called supercontinuum spectrum from the pump pulses to form stable broadband Stokes radiation so as to enable multiplexed CARS as described hereinbelow.

More particularly, an optical pulse source 30, embodied herein as a self mode-locked Ti:sapphire femtosecond pulsed laser such as the Spectra Physics Tsunami® Laser, and hereinafter referred to as the laser 30, emits a sequence of short optical pulses forming a laser beam 31. The term "femtosecond" in relation to a pulse is used to mean herein that the pulse duration is less than about 0.2 ps, and when used herein in relation to an optical source such as a laser means a source which in operation emits femtosecond pulses, i.e. pulses of duration less than about 0.2 ps. By way of example, the sequence of short optical pulses emitted by the laser 30 can have the following parameters: central wavelength $\lambda_0$~800 nm, repetition frequency F=80 MHz, pulse duration $\tau_0$=60 fs, pulse power P up to 0.5 W or less as required; in other embodiments, the pulsed laser 30 can emit pulses having other suitable values of $\lambda_0$, F, P, and $\tau_0$ as will be evident to those skilled in the art.

A beamsplitter 15 splits the laser beam 31 into two beams propagating along two different paths 20 and 21, which are referred to herein as Stokes and pump arms, respectively. A first beam is coupled into a first photonic crystal fiber (PCF) 14 that combines desired dispersive and nonlinear characteristics so as to form from received optical pulses an optical signal having a broad optical spectrum with a spectral lobe centered close to a desired Stokes wavelength $\lambda_S$.

In one embodiment, the PCF 14 has two zero dispersion wavelengths, i.e. wavelengths at which the chromatic dispersion of the PCF 14 is equal to zero, in the vicinity of the Stokes wavelengths $\lambda_S$, as described in a paper entitled "Optimization of coherent anti-Stokes Raman scattering microscopy using photonic crystal fiber", by S. Murugkar et al, presented at the Photonics North Conference, Ottawa, June 2007, which is incorporated herein by reference. By way of example, the PCF 14 is a photonic crystal fiber NL-1.4.775-945 available from Crystal Fiber, Inc of about 12.5 cm length, which has two zero dispersion wavelengths at 775 nm and 945 nm.

The PCF 14 is followed in the Stokes arm 20 by an optical spectral filter 34 having a passband centered at the Stokes beam wavelength $\lambda_S$, which produces a spectrally broad Stokes beam 9 centered at the Stokes wavelength $\lambda_S$ and formed by femtosecond optical pulses; this Stokes beam is then directed by a mirror 23 towards a beam combiner 11 in the form of a dichroic mirror for combining with a pump beam 10. The choice of the filter 34 depends upon which particular chemical bonds in sample molecules is to be imaged. By way of example, a filter 34 having a narrow passband of about 53 nm and centered at $\lambda_S \sim 1040$ nm will enable obtaining a CARS signal from C—H bonds in *cryptosporidium parvum* lipids, and therefore imaging of the lipid distribution in a sample. A more broadband filter, for example with a passband of about 200 cm$^{-1}$, will enable multiplexed CARS wherein a CARS spectrum is obtained without laser or filter tuning. In one embodiment, the filter 34 can be tunable, for example it can be in the form of an adjustable interference filter disclosed in U.S. Pat. No. 5,194,912 "Raman analysis apparatus".

The second part of the laser beam 31 from the beamsplitter 15 is directed along the pump arm 21 by a mirror 22, first to a chirp inducing element 13, which is embodied as a prism pair configured to impose a large negative chirp on the received optical pulses as known in the art; alternatively, other chirp inducing elements 13 can be used, such as a suitable grating stretcher as described in the paper "Optimization of coherent anti-Stokes Raman scattering microscopy using photonic crystal fiber", by S. Murugkar et al, which is incorporated herein by reference. The prism pair 13 is followed in the pump arm 21 by an optical element 12 having a suitably high chromatic dispersion, for example—another PCF. The PCF 12 receives chirped optical pulses from the prism pair 13 and generates therefrom spectrally narrow transform limited pump pulses of a picosecond duration; these spectrally squeezed pulses form the pump beam 10 having the pump wavelength $\lambda_p$, which in the exemplary embodiment described herein is equal to about 800 nm, and may have a spectral width which in one embodiment is at least 5 times less than the spectral width of the Stokes pulses to enable simultaneous detection of anti-Stokes signals at multiple frequencies. The pump arm 21 or the Stokes arm 20 may include a variable optical delay line to align the pump and Stokes pulses in time. The term "picosecond" in relation to a pulse is used herein to mean that the pulse duration is between about 1 ps and about 200 ps. The term "sub-picosecond" in relation to a pulse is used herein to mean that the pulse duration is less than 1 ps. By way of example, the Stokes pulses produced in the Stokes arm 20 can be of about 100 fs (femtosecond) duration and have a spectral width of about 200 cm$^{-1}$, while the pump pulses produced in the pump arm 21 can be of about 2 ps duration and have a spectral width of about 10 cm$^{-1}$.

The Stokes beam 9 propagating from the filter 34 and the pump beam 10 propagating from the PCF 12 are then directed onto a test sample 2 by optical means 11, 8, 27, and 3. In the shown embodiment the optical means for directing the pump and Stokes beams is formed by a beam combiner 11, an optional collimating lens or lens system 8, a scanning mirror assembly 27, and a first microscope objective 3. The beam combiner 11 may be embodied as a dichroic mirror and is disposed to combine the Stokes beam 9 and the pump beam 10 into a combined beam 111, which is also referred to herein as the combined CARS beam or CARS excitation beam, and is formed by the substantially overlapping Stokes and pump beams propagating coaxially. The scanning mirror assembly 27, for example utilizing a pair of galvanometer mirrors or a rotating micro-lens array disk such as those described in Microscopy and Microanalysis, Vol. 9 (Suppl. 2), 1090-1091, (2003), directs the combined beam towards the sample 2. The first microscope objective 3 is disposed for focusing the pump and Stokes beams into a small focal volume, preferably of the order of 1 µm$^3$ or less, at a particular location within the sample 2. Alternatively, a commercial microscope having beam scanning capability can be used in place of the elements 8, 27 and 3. In other embodiments, the apparatus can include means for moving the test sample 2 in two directions in a plane normal to the incident pump and Stokes beams as schematically illustrated by an arrow 25, so as to obtain a three-dimensional image of a portion of the sample 2, with a third dimension provided by varying a focusing depth of the microscope objective 3.

The CARS radiation, also referred to herein as the third radiation or anti-Stokes radiation, is generated due to nonlinear four-wave mixing in a location in the sample cell where the Stokes and pump beams are focused. Part of the CARS radiation propagates in the forward direction, i.e. in the direction of propagation of the Stokes and pump beams incident on the sample 2, and is collected by a second microscope objective 4, and is directed by a second beamsplitter 29 towards a first photodetector 61 and, optionally, to a spectrometer 71. An optical filter 51 is disposed in an optical path of the CARS radiation that passed through the sample 2, hereinafter also referred to as the forward detection path, to separate the CARS radiation from the radiation of the pump and Stokes beams, which is blocked by the second optical filter 51. Optionally CARS radiation propagating from the sample 2 in the reverse, i.e. epi-direction, is collected by the objective 3, and is then directed by an optional dichroic mirror 18 that separates the back-scattered CARS radiation from the pump and Stokes beams, to a second photodetector 62; the optical path of the back-scattered CARS radiation will be referred to herein as the epi-detection path. A second optical spectral filtered 52 can be disposed to filter out remaining Stokes and pump radiation and prevent it from reaching the second photodetector 62. The CARS radiation generated in the epi-direction may have a significantly higher signal to background ratio, but may also be smaller in intensity than that generated in the forward direction.

In one experimental embodiment of the apparatus shown in FIG. 3, a 700 nm short-pass optical filter from Chroma Technology Corp was used as the second optical filter 51, an Olympus 40×, 0.8 NA water immersion microscope objective was used as the microscope objective 4, and two different microscope objectives: Zeiss Plan Neofluar 16×, 0.5 NA and Zeiss Plan Neofluar 40×, 1.3 NA were used as the microscope objective 3 for low and high magnification images, respectively.

The photodetector 61, such as a Photo-Multiplier Tube (PMT) or an intensified CCD camera, is positioned for detecting the intensity of the CARS radiation generated at a particular location in the sample cell 2 for the purpose of generating one pixel of a CARS image. An optional narrow-band filter 53 centered at a desired anti-Stokes frequency can be provided before the detector 61 if a broadband Stokes signal is used, such as in the broadband multiplexed CARS. Electrical signals from the photodetector 61 are received and processed by a processor 33, which stores processed signals for a plurality of scanned locations in the sample 2 so as to form a CARS image of said sample or of a selected area therein. The processor 33 can be embodied as a general purpose processor equipped with a parallel data acquisition card, or as a suitable microprocessor, a DSP (Digital Signal Pocessor), an FPGA (Field Programmable Gate Array), any combination thereof, or any other digital processing means as would be known to those skilled in the art.

In the embodiment shown in FIG. 3, hereinafter referred to as a first embodiment, the pump beam 10 and the Stokes beam 9 are provided by a CARS optical source 32, which utilizes a single femtosecond pulse source 30 and two PCFs 14, and 12. Advantageously, this configuration enables an instantaneous detection of a CARS spectrum using a spectrometer 71 as described hereinbelow. However, the CARS optical source 30 can also have alternative embodiments.

Figure 4:
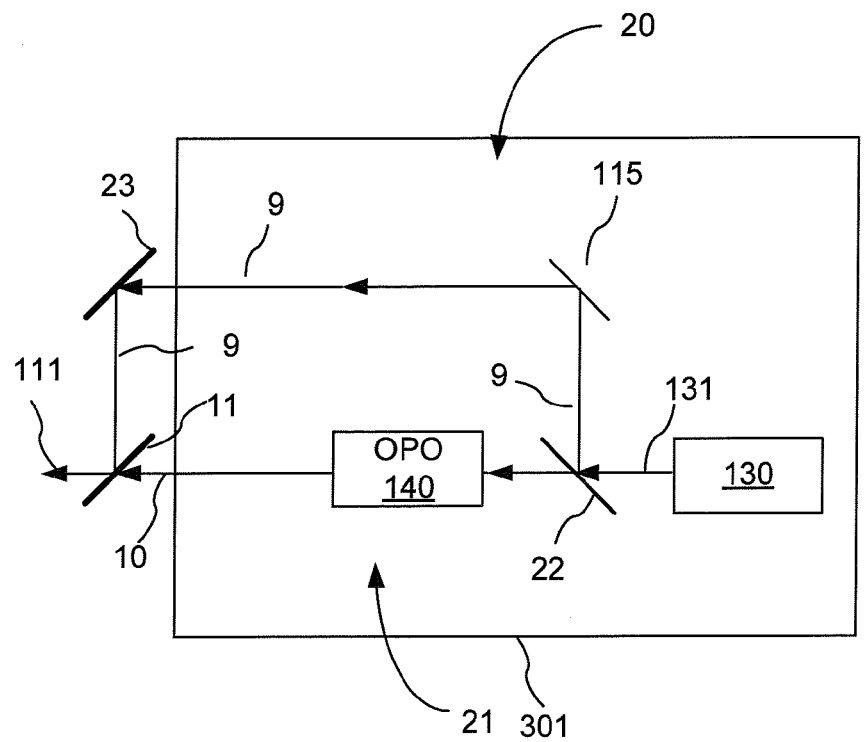
FIGS. 4 and 5 are schematic block diagrams of two alternative embodiments of a CARS optical source for emitting pump and Stokes beams for use in the apparatus of FIG. 3.

A second alternative embodiments of the CARS optical source is illustrated in FIG. 4 wherein it is indicated as 301. In this embodiment, a smaller fraction of optical radiation 131 generated by a single picosecond laser 130 is split-off by a beam splitter 22 and a folding mirror 115 and used to form the Stokes beam 9, while a larger fraction of the Laser 130 output is used to drive an OPO (optical parametric oscillator) 140 for producing the pump beam 10. Such a source is described, for example, in an article by F. Ganikhanov, S. Carrasco, X. S. Xie, M. Katz, W. Seitz and D. Kopf, "Broadly tunable dual-wavelength light source for coherent anti-Stokes Raman scattering microscopy", Optics Letters 31, 1292-1294 (2006), which is incorporated herein by reference.

Figure 5:
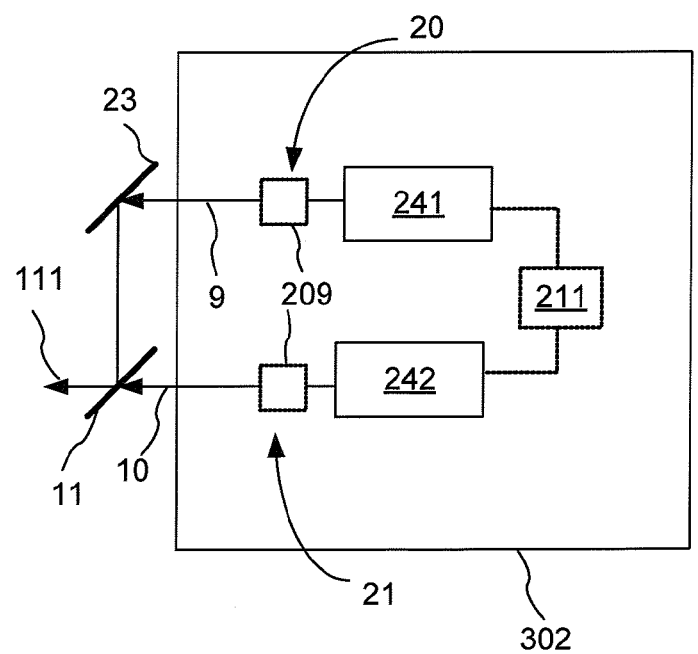

A third alternative embodiment of the CARS optical source is illustrated in FIG. 5 wherein it is indicated as 302. In this embodiment, two distinct pulsed lasers 241 and 242 are phase locked using a phase locker 211, and are used for generating the Stokes beam 9 and the pump beam 10, respectively.

EXAMPLE 1

Experiments were performed to illustrate the invention. The experimental setup was similar to the apparatus shown in FIG. 3, and utilized the CARS optical sources as illustrated in FIGS. 4 and 5.

A first experiment involved a Nd:vanadate laser 130 from High-Q Laser (Hohenems, Austria) disposed as illustrated in FIG. 4; in operation it emits radiation 131 with an output power of 10 W at 1064 nm with a pulse duration of 7 ps and a repetition rate of 76 MHz. A portion of the output 131 is split off using a power splitter 22 and used as the Stokes beam 9. The remaining 9 W is used for synchronously pumping an optical parametric oscillator (OPO) 140 (Levante, APE, Berlin) to generate the pump beam 10, which is then combined with the Stokes beam 9 to form a combined CARS excitation beam 111. The OPO signal is intracavity doubled to produce narrow spectral bandwidth radiation wavelength tunable between 780 nm and 930 nm in the form of a stream of optical pulses having a spectral bandwidth of about 3.5 $cm^{-1}$ with pulse duration of ~5 ps and an average output power of ~1.5 W at 76 MHz pulse repetition rate. These parameters assure a suitably high spectral resolution and a high signal to background ratio.

An alternate light source for pump and Stokes beams as illustrated in FIG. 5 was available in the experimental setup as well. This CARS optical source 302 incorporated two Ti:sapphire lasers Tsunami® 241, 242, which are available from Spectra-Physics, Mountain View, Calif., emitting two 5 ps optical pulse trains that are synchronized to an 80 MHz clock using a "Lok-to-Clock" feature from Spectra Physics schematically illustrated in FIG. 5 at 211, said optical pulse trains forming the pump beam 10 and the Stokes beam 9. The timing jitter between the pulses of the pump and Stokes beams was about 0.5 ps. The pump beam 10 is tunable from 700 to 840 nm and the Stokes beam 9 from 780 nm to 900 nm, each with a maximum time-averaged output power of ~1 W.

The divergence of the pump and Stokes beams is controlled by a telescope 209 in each beam path, while a delay line, which is not shown, is used to provide temporal overlap of the two pulse trains. The pump and Stokes beams are coaxially combined using the dichroic mirror 11, and the combined beam 111 directed to a laser-scanning microscope (Olympus FV300/IX70) that is modified for CARS microscopy. A pair of galvanometer mirrors in the microscope controls the scanning of the two beams on the sample surface. The pump and Stokes laser beams are focused onto the sample using a water objective lens (UPlan/APO, 60×, Olympus America, Inc.) with a numerical aperture (NA) of 1.2 as the microscope objective 3 illustrated in FIG. 3. The forward CARS radiation is collected with an air condenser lens (NA=0.55) as the microscope objective 4, is separated from the excitation pump and Stokes beams using a dichroic mirror (Chroma, Brattleboro, Vt.) as the optical filter 51, and is further filtered using the filter 53 to reject the residual excitation beams and finally detected using a photomultiplier tube (PMT) (model R3896, Hamamatsu) as the photodetector 61. The set-up provided a spatial resolution of about 0.2 μm which benefited from the optically non-linear character of the CARS effect.

The frequency difference between the pump and Stokes beams 10, 9 is set so that it matches the molecular vibration frequency of the aliphatic C—H vibrations at 2845 $cm^{-1}$ of lipid molecules. This requires tuning the pump beam 10 in the case of the OPO setup 301 to 816.9 nm when the Stokes beam 9 is at 1064 μm. In the case of the setup 302 with the two synchronized Ti:sapphire lasers 241, 242, the wavelengths of the pump and Stokes beams 10, 9 are 716.8 nm and 900.4 nm, respectively. The optical power of the pump and Stokes beams radiation at the sample, hereinafter also referred to as the first and second radiation respectively, was ~24 mW for the pump beam and ~28 mW for the Stokes beam, respectively when using the synchronized Ti:sapphire lasers system 302, and were about 75 mW for the pump beam and ~38 mW for the Stokes beam when using the OPO based system 301.

Samples of live (viable) *Cryptosporidium parvum* oocysts originating from experimentally infected calves (Iowa isolate) were obtained from Waterborne, Inc. of New Orleans, La., U.S.A. The oocysts were suspended in a solution of phosphate-buffered saline (PBS) with antibiotics and a non-ionic surfactant and emulsifier Tween® 20. Due to the hazardous nature of the sample, all sample preparations and imaging experiments were performed in a bio-safety level 2 accredited laboratory environment. A couple of drops of the PBS solution containing the *cryptosporidium parvum* oocysts were placed on top of a microscope slide and covered with a thin coverslip.

FIGS. 6A and 6B show close-up views of typical CARS images of small areas in the sample where live *cryptosporidium parvum* oocysts were found. The image in FIG. 6A was obtained in the forward direction (F-CARS) using the CARS optical source 302 based on synchronized Ti:sapphire lasers. This image, averaged over two frames, is cropped out of a bigger image that is 512×512 pixels in size corresponding to an area of ~125 μm×125 μm. The acquisition time for this image was about 2 second. An image artifact 610 is clearly visible on a dark background in the center of FIG. 6A as a dim diffuse circular feature of about 5 μm in diameter with a bright ~1 μm spot 615 inside; it has a pattern, size a shape that is characteristic to a CARS image of a *cryptosporidium parvum* oocyst and indicates the presence thereof.

The image in FIG. 6B was obtained in the forward direction (F-CARS) using the OPO based CARS optical source 301.

The shorter wavelength of the pump in FIG. 6A results in a higher resolution image. A similar image artifact 620 clearly visible on a dark background in the center of FIG. 6B as a dim diffuse elliptical feature of about 5 µm in a large diameter with a bright ~1 µm spot 625 inside; it has the same pattern, size a shape that the image artifact shown in FIG. 6A which is characteristic to a CARS image of a *cryptosporidium parvum* oocyst, and therefore indicates the presence thereof.

It is clearly evident from FIGS. 6A,B that there is a strong CARS intensity associated with a spherical structure of about 1 µm in diameter within each of the image artifacts, indicating a high lipid density. The circular or slightly elliptical area of about 5 µm in diameter surrounding this feature contributes a weaker CARS signal. The intensity profile along a line AA drawn across the image in FIG. 6B is shown in FIG. 6C; it is characterized by a strong peak of about 1 µm+\-0.5 µm in width on a pedestal of about 5 µm+\-1.5 µm width. This morphology is consistent with the structure of *cryptosporidium parvum* oocyst obtained by electron microscopy, see for example F. Petry, Microscopy and Microanalysis, 10, 586-601, (2004). The high lipid density seen as the 1 µm bright spots 615, 625 corresponds to a lipid vacuole inside the residual body. Along with the amylopectin granules, this lipid vacuole acts as the source of nutrition for the sporozoites inside the oocyst.

This feature consisting of the 1 µm bright spot in the 5 micron circular area is used in one embodiment of the present invention as an identifying pattern in an algorithm for image recognition of *cryptosporidium parvum* oocyst. When the frequency difference of the excitation beams is tuned to be off-resonance, for example at 2750 cm-1, the contrast in the CARS image disappears and not much signal is obtained.

Figure 7:
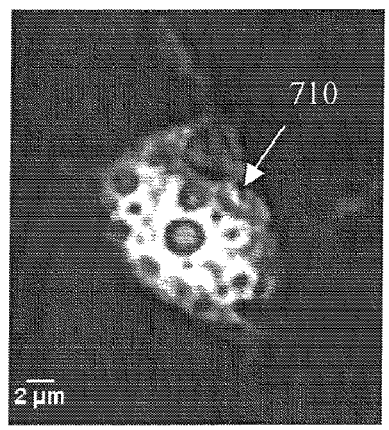
FIG. 7 is a CARS image showing a non-viable cysts of *Giardia lamblia*.

FIG. 7 shows a close-up views of an F-CARS image of a small area in a sample comprising non-viable (dead) cysts of *Giardia lamblia* dried on top of microscope well slides. The sample was obtained from GAP EnviroMicrobial Services (London, ON, Canada) with the OPO based system with the pump-Stokes frequency difference tuned to 2845 cm-1. A bright image artifact 710 with a characteristic size of about 10-15 µm clearly visible in the central are of the CARS image in the figure corresponds to a single cyst of *Giardia lamblia*. The shape and pattern of the image artifact in FIG. 7 indicates that the lipid distribution in a *Giardia* cyst is very different from that of crypto oocyst. The size of ~14 micron of the *Giardia* cyst and the observed structure is consistent with reports in literature, see for example Microscopy and Microanalysis 10, 513-527, 2004.

Figure 8:
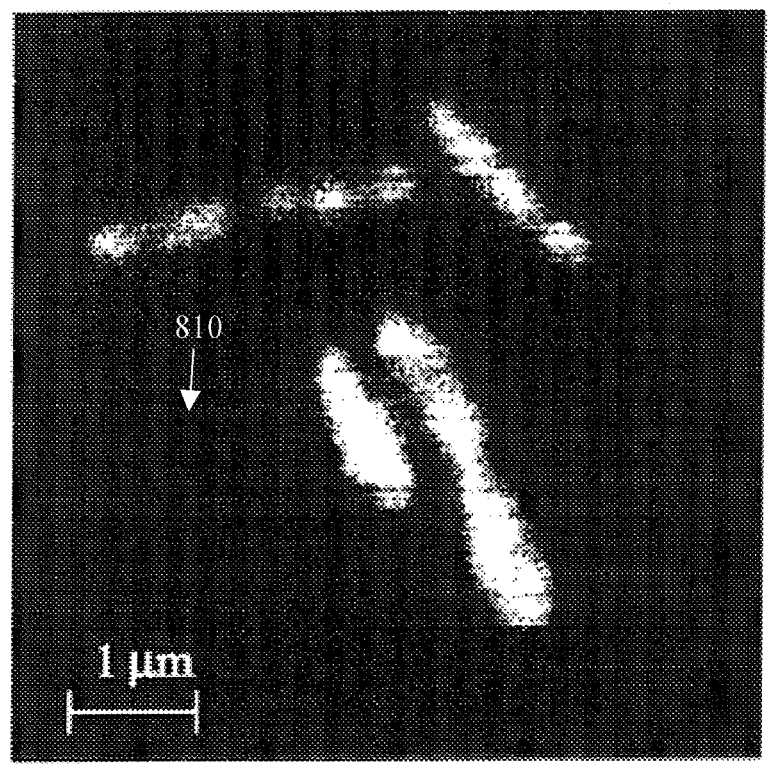
FIG. 8 is a prior art CARS image of six live, unstained bacteria of the type *Shewanella putrefaciens*, strain CN-32.
Figure 9:
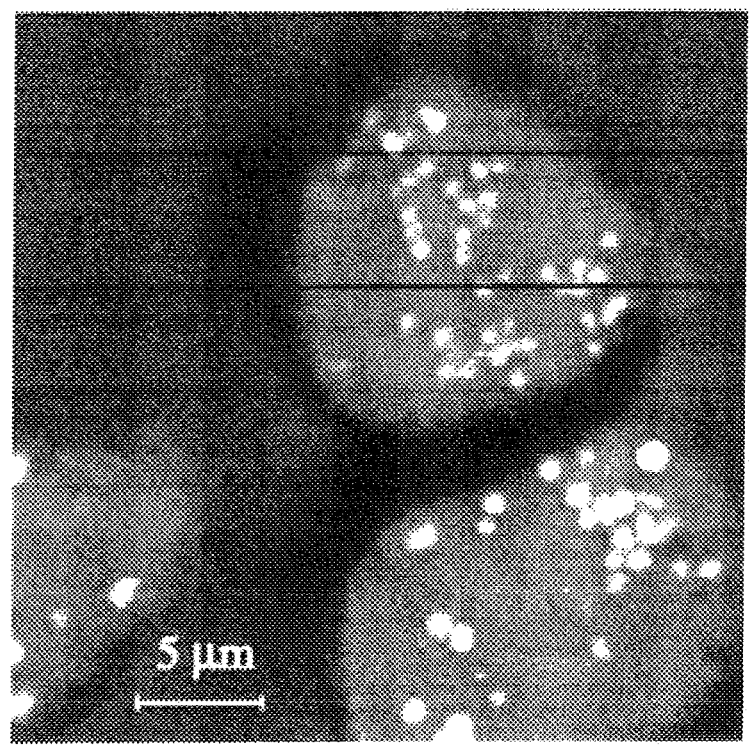
FIG. 9 is a prior art CARS image of three live, unstained HeLa cells in aqueous HEPES buffer solution.

To illustrate that the characteristic pattern, size and shape of a CARS image of a *cryptosporidium* oocyst is easily discernable from other microorganisms, CARS images of six live bacteria of the type Shewanella putrefaciens, strain CN-32, in D2O is shown in FIG. 8, which reproduces FIG. 7 of U.S. Pat. No. 6,108,081, while FIG. 9 shown CARS images of three live, unstained HeLa cells in aqueous HEPES buffer solution. Clearly, CARS imaging of these microorganisms yield image artifacts that differ in shape, pattern and size from image artifacts produced by the CARS interaction in the *cryptosporidium* oocyst. Note that in the context of this specification, the term "image artifact" is a compact discernable feature in a CARS image of a sample that may be related to a micro-object in the sample.

Real-Time Trapping and Automated Identification

One important advantage of the system and method for a pathogen detection of the present invention is that the CARS signal is generally several orders of magnitude stronger under similar conditions than the spontaneous Raman signal used in the prior art. This is due to the coherent nature of the CARS process, wherein the frequency-shifted anti-Stokes signal is a result of a constructive interference of the Stokes and pump radiation, which gives rise to a significantly higher intensity of the CARS radiation compared to the Raman radiation. Additionally, the collection efficiency of the CARS radiation is also much higher due to the directional nature of the CARS signal as defined by the phase matching requirement for the four-wave mixing process that produces the CARS radiation.

Accordingly, the acquisition time for a typical image in the CARS-based system of FIG. 3 is reduced to about a second or less as compared to many hours that are typically required to acquire a comparable image in Raman microscopy; according to the present invention, it can be reduced even further using parallel acquisition of a plurality of pixels of on CARS image as described hereinabove.

Another significant advantage of using CARS microscopy for detection of waterborne pathogens in water samples is that the sample does not need any extra or complicated preparation. The sample for assessment of pathogens may contain water or any physical or chemical medium used for the concentration of pathogens without destroying them. This enables to use the CARS-based method of the present invention for real-time automated detection of pathogens in water supplies, as described hereinbelow. If the CARS spectrum of the medium is known, a significant improvement in the signal to noise ratio is obtained by avoiding tuning to the vibration frequencies of the medium that may overlap with those of the pathogen, and/or by subtracting the known CARS signal of the medium from the measured CARS signal.

Accordingly, the present invention enables a rapid detection of a single pathogen organism, such as a single oocysts, without any complicated sample preparation. This for the first time enables real-time or almost real time water monitoring for the presence of water-borne pathogens and automated identification of the detected pathogens while resolving individual organisms. One exemplary embodiment of such a water monitoring apparatus in shown in FIG. 11 and is hereinafter described.

Figure 11:
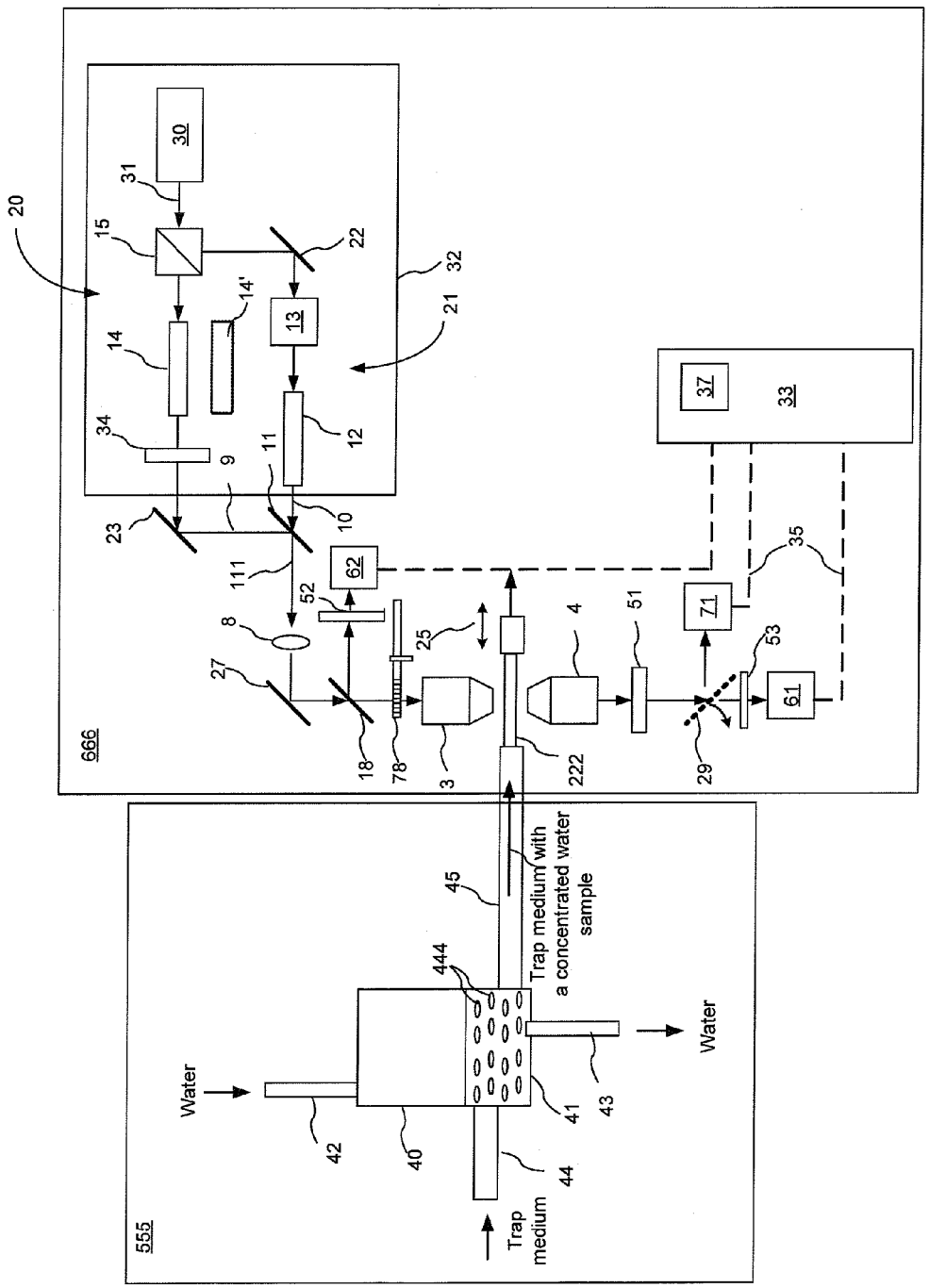
FIG. 11 is a block diagram of a system for automated real-time water monitoring according to the present invention.
Figure 12:
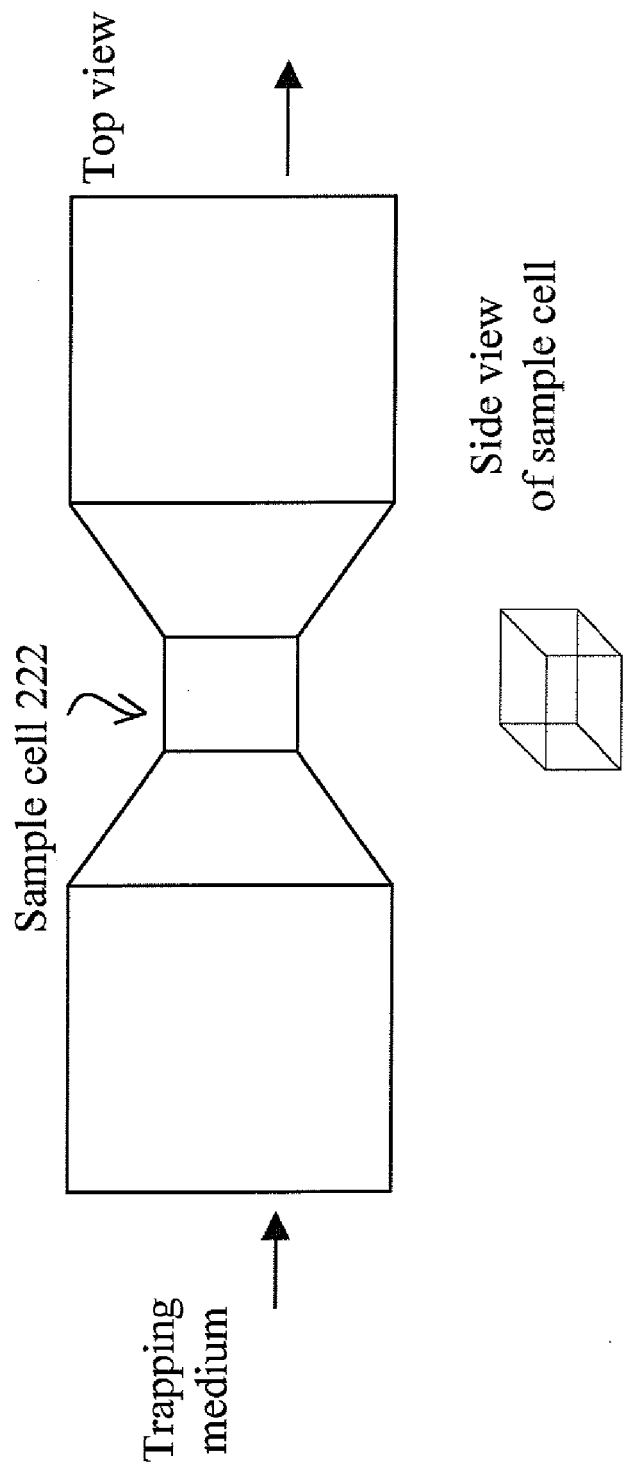
FIG. 12 is a schematic illustration of one embodiment of a sample cell that can be used in the system of FIG. 11.

The system shown in FIG. 11 includes a pathogen accumulator 555 wherein a water sample is prepared, and a CARS apparatus 666 for pathogen detection, which may be similar or identical to that shown in FIG. 3, but as shown includes also an optional spinning micro-lens array disk 78 as described hereinbelow. The CARS apparatus 666 is also referred to herein as the CARS imager. A water container 40 has a water inlet pipe 42 and a water outlet pipe 43 for directing water under test in and out of a container 40 which has a lower container section 41 supporting a trapping medium 444. The container 40 also has trapping medium guides 44 and 45 for slowly guiding the trapping medium through the container 40 and for directing the trapping medium 444 out of the water and into a sample cell 222. The pathogen accumulator 555 can have other means for automatically directing the trapping medium 444 out of the water container 40 and into the sample cell 22 of the CARS imager without human intervention, such as suitable pumps, flow meters, flow regulators and the like, which may depend on a particular implementation of the trapping medium and would be evident to those skilled in the art. The water continuously flows through the trapping medium 444 contained in the lower section 41 of the water container 40 at a water flow rate that is controlled for example by a peristaltic pump and a flow meter with a valve that are not shown. The water flow rate depends on the trapping medium and by way of example can be in the range of 0.4-4 L/minute. The trapping medium 444 flows through the container 40 into a sampling cell 222 at a much slower rate, for example about 10 μL/second. The sampling cell 222 may be made of transparent quartz glass and may be for example as shown in FIG. 12.

The trapping medium functions to trap waterborne pathogens such as *cryptosporidium parvum* oocysts so that they can be accumulated therein, forming a sample that may have pathogen concentrations exceeding the pathogen concentration in the water by up to $10^6$ times. One example of a suitable trapping medium is Diatomaceous earth (DE), which is an organic microporous material that is commonly used in water filtration methods for trapping contaminants in water. Certain products such as chemically treated DE manufactured by EcoVu Analytics (Ottawa, ON, Canada) can enhance the trapping efficiency of DE by up to 10,000 times; this type of trapping medium is described in U.S. Pat. No. 5,512,491, which is incorporated herein by reference. In one embodiment that will be described hereinbelow, the trapping medium 444 is a slurry made of such a chemically treated DE and reagent water. An example of reagent water is de-ionized (DI) water which is known to be free of pathogens such as oocysts and cysts and other interfering materials so as not to introduce contaminants in the water being tested.

In one embodiment, the trapping medium 444 continuously flows through the sample cell 222 while the CARS images and spectra are taken as described hereinabove with reference to FIG. 3. In another embodiment, once the cell 22 is filled with the trapping medium carrying a sample to be tested, the flow of the trapping medium is stopped while the sample cell volume is imaged. Once all the CARS measurements on the trapping medium within the cell 222 are finished, the flow of the trapping medium is resumed until the cell 222 is filled with a new portion of the trapping medium. By way of example, the cell 222 may have internal dimensions of 200 μm×200 μm×100 μm, with the last dimension being the cell height in the direction of pump and Stokes beams propagation, which corresponds to the cell volume to be imaged of about $4\times10^{-6}$ cm$^3$.

EXAMPLE 2

Figure 10:
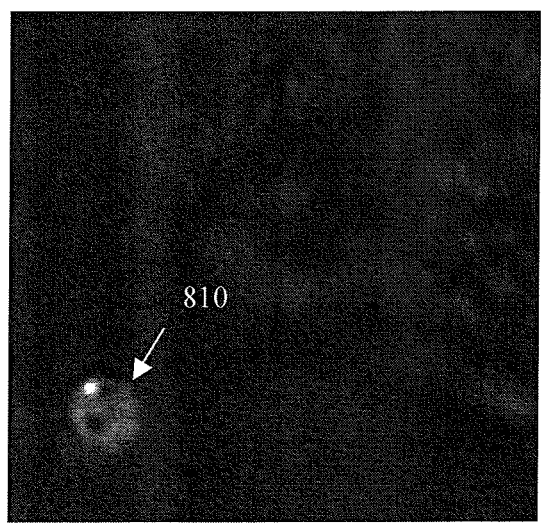
FIG. 10 is an image of live *cryptosporidium parvum* oocyst in aqueous organic trapping medium.

An experiment was conducted to demonstrate the feasibility of detecting a pathogen using CARS microscopy in the presence of a trapping medium. For this purpose, a sample of the organic trapping medium was obtained from EcoVu Analytics (Ottawa, ON, Canada). A small amount of this trapping medium was mixed with water and the slurry placed on a microscope glass slide. A drop of the PBS solution containing live *cryptosporidium parvum* oocysts was added to this. This sample was covered with a thin glass coverslip and imaged in the forward direction. Resulting CARS image is shown in FIG. 10. An image artifact 810 having the characteristic pattern, shape and size of an individual *cryptosporidium* oocyst is clearly discernable in the left hand bottom corner of the image. This image artifact visualizes the same lipid density pattern corresponding to the *cryptosporidium parvum* oocyst as described in EXAMPLE 1 and shown in FIGS. 6A,B. This pattern consists of the 1 μm bright spot in the 5 micron circular area. A weaker non-resonant CARS signal, which is not related to the lipid molecular vibrations and arises mainly due to electronic excitations from the surrounding trapping medium, is seen in the CARS image of FIG. 10. This non-resonant background signal can be mostly suppressed using, for example, frequency modulation CARS (FM-CARS) as described for example by F. Ganikhanov et al, Optics Letters, 31, No. 12, 1872-1874 (2006), leaving only a resonant CARS signal from the pathogen. Therefore, a pathogen trapped in the aqueous trapping medium can be successfully identified using CARS imaging of the trapping medium.

Turning back to FIG. 11, the CARS apparatus 666 may use the pump and Stokes radiation to illuminate the trapping medium within the cell 222, which in this case serves as the sample, at a single focal location at a time; in such an embodiment it forms CARS images sequentially pixel by pixel, changing the focal location within the sample between individual pixel acquisitions by means of scanning the combined beam across the cell 222. This method may provide imaging time of about 1 image frame per second. However, commercially available optical sources that can be used in CARS often have maximum output power that far exceeds power requirements to the pump and stokes beams for CARS signal generation.

Figure 13:
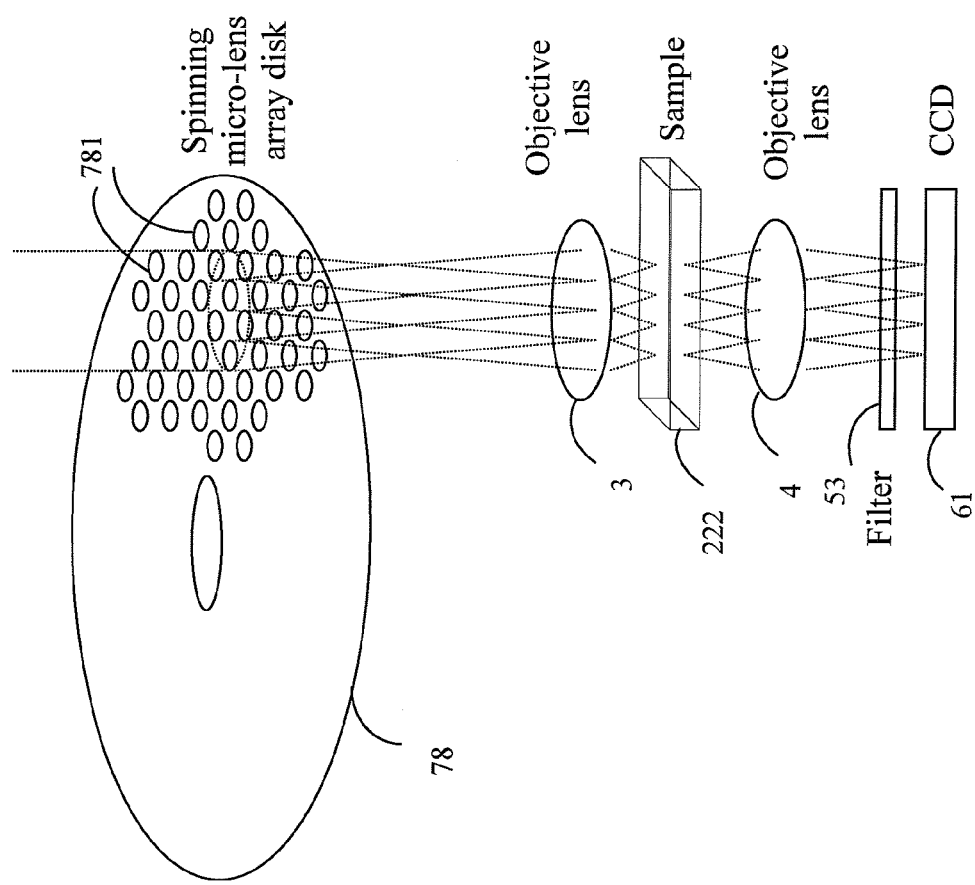
FIG. 13 is a schematic diagram illustrating the use of a spinning micro-lens disk array in the system shown in FIG. 11.
Figure 14:
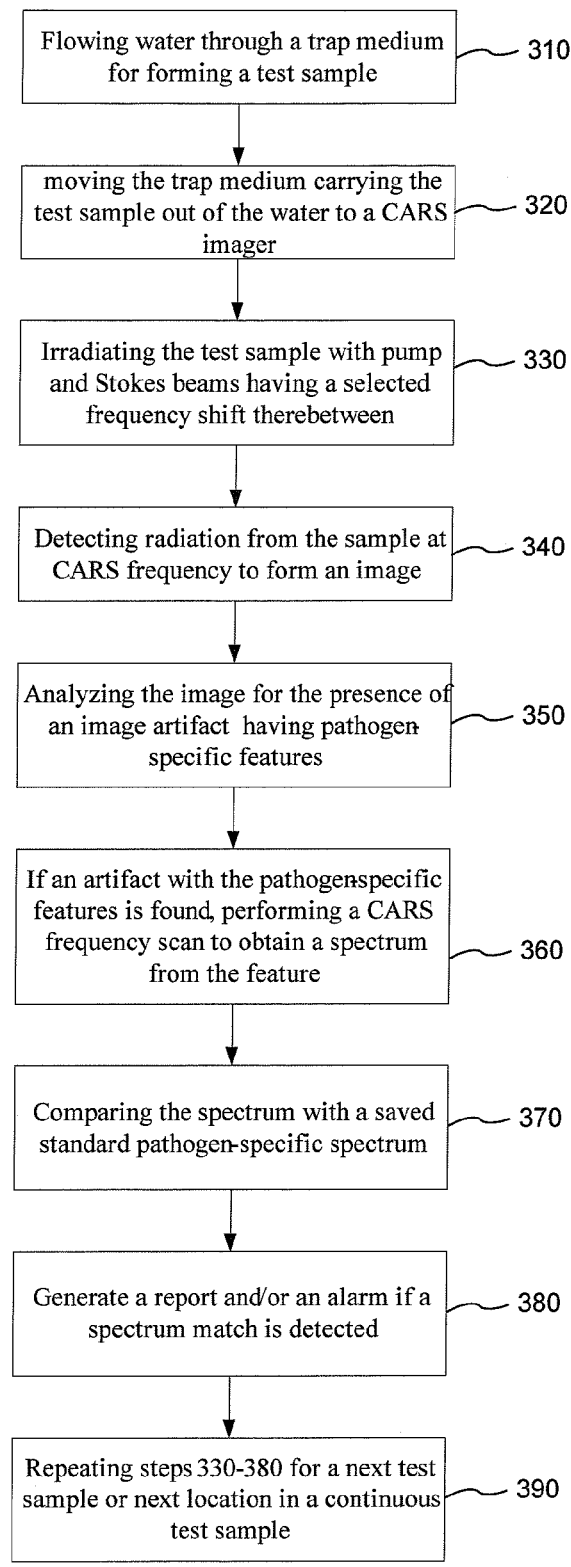
FIG. 14 is a flowchart showing general steps of the method of water monitoring for the presence of a pathogen according to one embodiment of the present invention.

Therefore, in a preferred embodiment, the CARS apparatus 666 includes means for parallel CARS signal acquisition, when several pixels of a CARS image are simultaneously acquired. This means may include utilizing an array of micro lenses and a matching photodetector array having at least as many elements as the array of micro-lenses as the photodetector 61. In the embodiment shown in FIG. 12, a spinning micro-lens array disk (MLAD) 78, which is available commercially from, for example, Yokogawa Electric Corporation, Japan, is disposed between the objective 3 and the dichroic mirror 18, and is complemented with a CCD camera as the photodetector 61. This optical arrangement is schematically illustrated in FIG. 13, which shows a sample illumination arrangement of the CARS apparatus 666 of FIG. 11, from the spinning MLAD 78 down to the photodetector 61.

The MLAD 78 includes a plurality of microlenses 781 arranged in a spiral pattern to raster scan the sample cell with multiple light beams focused by the micro-lenses into a plurality of small, preferably about 1 μm$^3$ or less, focal volumes in a plane that is imaged by the objective 3 onto a focal plane within the sample cell 222. When the MLAD 78 is spinning, the plurality of small focal volumes whereupon portions of the combined excitation beam 111 are focused scan the trapping medium within the sample cell 222. Resulting CARS radiation is collected and focused onto a plurality of pixels of the photodetector 61 embodied herein as a CCD array, for example—as an electron multiplying CCD camera (EM-CCD) having 1024×1024 detector pixels, which is available for example from Andor Technology, Belfast, Northern Ireland.

By way of example, the sample cell has a square 200 μm×200 μm cross-section in a plane normal to the combined beam 111 direction, and has a thickness of 100 μm. The combined excitation beam 111, optical power 1 W, illuminates a spot on the MLAD 78 of about 200 μm in diameter, while the diameter of each microlens of the MLAD 78 is 40 μm, illuminating up to about 18 distinct focal locations within the sample cell 2 simultaneously and providing about 40 mW of excitation power at each of these focal locations. In operation, the MLAD 78 rotates at a rotation speed of about 5000 rpm or about 83.3 rps (rotations per second), and raster scans a 200 μm×200 μm field of view within the sample cell 2 with a 0.5 μm spatial resolution when rotated at about 30 degrees, so that there are 12 scans/rotation, providing an imaging speed of up to 1000 frames per second.

In this example, total time required to image the full volume of the sample cell 222 is about 100 millisecond, including 100 depth scans. If the time it takes for the trapping medium to fill the sample cell 222 is sufficiently short, this embodiment of the system of the present invention provides real-time testing of the trapping medium flowing through the sample cell 222 at an average flow rate of about $4\times10^{-5}$ cm$^3$ per second. Accordingly, it will take about 42 minutes to test 0.01 cc of the trapping medium, about the amount contained in one drop, corresponding to a water volume of about 1 cc to 100 cc assuming the pathogen concentration factor provided by the trapping medium is 100 to 10000. This advantageously compares to several days that are typically required to fully analyze this amount of water for the presence of water-borne pathogens using conventional anti-gene labeling methods, and tens of hours that would take to analyze the same amount of sample water using the prior-art Raman method. As an example, USEPA method 1623, that requires that a test sample of 100 mL (=100 cc) be analyzed for *e-coli* bacteria by mean of a visual analysis of a specially prepared sample by a skilled technician, typically takes up to one week to perform.

According to another aspect of the present invention, the exceptionally fast image acquisition provided by the CARS apparatus 666 is supported by automated assessment of acquired images for the presence of pathogen signatures. This assessment is performed by the processor 33 as described hereinbelow.

Turning back to FIG. 11, electrical signals representing individual image pixels are provided by the CCD 61 to the processor 33 during or at the end of each raster scan. The processor 33 forms from said signals individual images, and automatically analyzes each obtained image in real time for the presence of image artifacts characteristic to a particular pathogen. The processor 33 can also be programmed to first perform suitable image processing to reduce image noise and/or remove non-resonant CARS background and/or image features related to CARS signals from the trapping medium or other known non-pathogenic water contaminants.

In one embodiment, the processor 33 includes a memory 37 for storing a database of reference CARS images taken at one or more specific CARS frequencies for a plurality of pathogens and/or other waterborne microorganisms, and is programmed to compare obtained CARS images with the reference images stored in the database.

According to a preferred embodiment of the invention, the processor 33 is programmed to analyze the image to assess occurrence of one or more image artifacts having a shape, size or intensity pattern that is characteristic to a CARS image of a particular pathogen, and if more that one such artifact is identified, to count the artifacts matching the pre-determined criteria to determine the number of the pathogens in the sample.

Figure 15:
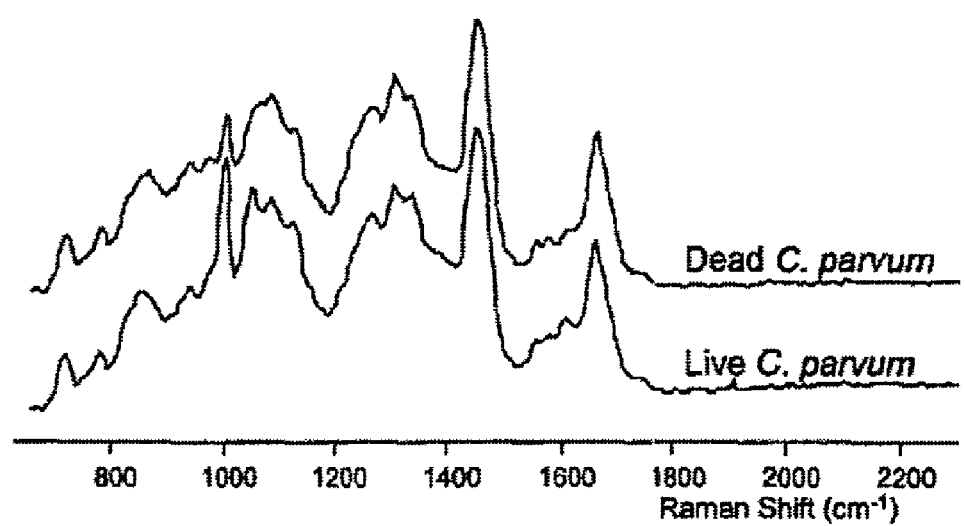
FIG. 15 is a prior art plot showing Raman spectra of viable and non-viable *cryptosporidium parvum* oocysts.

In one embodiment, the method of pathogen identification according to the present invention includes the following steps:

a) A CARS image of a calibration sample of the trapping medium without water-borne pathogens and other contaminants is obtained and stored in memory 37 of the processor 33 as a calibration image;

b) the sample cell 222 is filled with the trapping medium 44 carrying a concentrated water sample as described hereinabove;

c) A CARS image of the trapping medium within the sample cell is obtained as described hereinabove;

d) The stored calibration image obtained in step (a) is subtracted from the CARS image obtained in step (c) to obtain a calibrated CARS image;

e) The calibrated CARS image is analyzed for the presence of image artifacts having pre-determined features characteristic to a specific pathogen. Standard methods in image recognition such as image segmentation may be used in this step to distinguish pathogens based on the CARS intensity profiles. For example, as seen in the images in FIGS. 6A, 6B and 10, features of a CARS intensity profile of a single *cryptosporidium parvum* oocyst at 2845 cm-1 CARS shift include a peak with FWHM of 1 µm+\-0.5 µm on a pedestal of about 5 µm+\-2 µm wide; this intensity pattern is unique to *cryptosporidium parvum* oocyst and are used in the invention to identify this pathogen. Different pathogens have different CARS intensity profiles/patterns as seen in FIG. 7-9 described hereinabove. A library of such CARS images of various pathogens is collected and stored in the processor memory.

f) If the calibrated image is determined to contain an artifact matching one or more pre-defined criteria and/or one of the stored reference CARS images, a CARS spectrum of the pathogen in a "fingerprint region" of CARS frequency shifts is automatically collected; in a preferred embodiment this fingerprint region is between 600 cm$^{-1}$ and 1800 cm$^{-1}$, but may differ therefrom, for example depending on particular pathogens being analyzed. In one embodiment, if an image artifact matching a reference image or other pre-determined criteria for a given pathogen is detected, the CARS radiation from a sample location corresponding to the artifact is re-directed to a spectrometer 71 using a flip mirror 29, and a CARS spectrum is detected. In an embodiment wherein the pump and/or stokes beams are generated using tunable lasers, for example as illustrated in FIGS. 4 and 5, this CARS spectrum can be obtained by varying one of the pump or Stokes wavelengths in response to a control signal generated by the processor 33. Alternatively, the CARS apparatus 666 may utilize the broadband multiplexed CARS as described hereinabove, which employs broad bandwidth Stokes pulses and spectrally narrow pump pulses to obtain broadband anti-Stokes radiation, herein termed CARS radiation, which spectrum can then be directly analyzed for the presence of molecular vibrational resonances within the bandwidth of the Stokes radiation. This approach not only reduces the time for obtaining the CARS spectrum, but also gives more accurate information on ratio of intensities of CARS signal at two or more frequency shifts in the spectrum, and provides a greater accuracy in pathogen identification based on multivariate analysis methods. In one embodiment, optional optical switches within the Stokes arm 20, which are not shown, can be used to direct light from the laser 30 to pass through an alternative PCF 14' instead of the PCF 14 during the CARS spectrum acquisition, in order to spectrally broaden the Stokes pulses so as to generate the required "fingerprint" spectral region, e.g. from 600 cm$^{-1}$ to 1800 cm$^{-1}$, in the CARS signal.

g) The detected CARS spectrum is then compared to a stored reference spectrum for the respective pathogen or, to a library of stored spectra for a plurality of known pathogens or other contaminants. In another embodiment, the Raman spectrum is first retrieved from the CARS spectrum, for example using a method described in E. M. Vartianen et al, "Direct extraction of Raman line-shapes from congested CARS spectra", Optics Express 14, 3622 (2006), and is compared to a library of Raman spectra from various known waterborne pathogens; this method can be initially preferred since reference Raman spectra are currently more readily available than reference CARS spectra of pathogens. Determining whether the recorded CARS spectrum matches any of the stored reference spectra can be performed using a variety of known mathematical algorithms implemented as computer instructions, which would be apparent to a skilled practitioner; for example, this step can utilize well-known multivariate analysis techniques. By way of example, FIG. 15 illustrates spontaneous Raman spectra that could be contained in the computer memory. It shows Raman spectra of live (bottom curve) and dead (top curve) *cryptosporidium parvum* oocysts in the "fingerprint region" of 600 cm-1 to 1800 cm-1, reproduced from U.S. Pat. No. 6,950,184. An intensity ratio of peaks at about 1000 cm-1 and 1050 cm-1, the former corresponding to DNA backbone stretching vibrations, is different in the live *cryptosporidium parvum* oocysts as compared to the dead oocyst, and can be used for a positive identification whether a detected image artifact matching *cryptosporidium parvum* oocyst is produced by a live or dead *cryptosporidium parvum* oocyst. Accordingly, this step could be used as an indicator of oocyst viability, in addition to identifying the *cryptosporidium parvum* oocyst.

h) If a match is found between a Raman spectrum stored in memory and the CARS spectrum measured from the location of the suspect pathogen in the sample, a pathogen report and/or alarm is generated.

According to the invention, the aforedescribed steps (d)-(h) are performed or coordinated by the processor 33, which is also referred to herein as the computer and includes stored computer instructions for performing these tasks automatically in real time without human intervention, preferably for each generated image while the images are generated by the CARS apparatus 666, thereby advantageously enabling automated real-time pathogen detection and identification.

Accordingly, the CARS-based pathogen detection system and method of the present invention enables real-time water monitoring for the presence of water-borne pathogens, while simultaneously enabling automated detection and authentication of the pathogens.

Note that the exemplary embodiments of the system and method of the present invention described are by way of example only, and alternative embodiments of many elements and steps can be employed in particular applications of the invention as would be evident for those skilled in the art.

For example, the trapping medium 444 can include various trapping materials and can be chemical trapping medium or physical trapping medium, liquid or solid, for example based on microporous materials capable of trapping pathogens preferably without destroying them. In one embodiment, the trapping medium is liquid and continuously flows through the sample cell during the CARS imaging at a known flow rate, and the processor 33 can be programmed to account for the sample movement between successive pixel acquisitions so as to correct for image distortions due to the sample flow.

In another embodiment, the flow of the trapping medium 444 is stopped while the CARS images of the sample volume are acquired, after which the sample cell 222 is refilled.

In yet another embodiment, the trapping medium 444 is a substantially solid microporous filter, for example in the form of a continuous sheet that is slowly pulled through the water container 40, where it acquires a concentrated water sample, i.e. water contaminants such as pathogens and microscopic amount of water trapped by the trapping medium, and is then provided at a predetermined rate or at predetermined intervals to the CARS apparatus 666. In an embodiment wherein the trapping medium is solid, it may have a specially prepared surface such as that used in surface enhanced Raman scattering (SERS) for enhancing the CARS signal.

General steps of the method of the present invention for assessing the presence of a pathogen in water according to a preferred embodiment thereof are summarized in a flowchart shown in FIG. 14. As shown, the method includes:

Flowing water to be analyzed through a trap medium in a first step 310 to form a water sample wherein pathogens may be concentrated;

In a next step 320, continuously or sequentially moving the trap medium carrying the test sample out of the water to a CARS imager;

In a step 330, irradiating the sample with first, i.e. pump, radiation having a spectrum centered at a first frequency and second, i.e. Stokes, radiation having a spectrum including a second frequency, wherein the first frequency exceeds the second frequency by a pre-determined non-zero frequency shift characteristic to the pathogen;

In a step 340, detecting third, i.e. anti-Stokes or CARS, radiation scattered from or transmitted through the sample at a third frequency that is different from the first and second frequencies, so as to form an image of at least a portion of the sample;

In a step 350, analyzing the image to assess occurrence of at least one image artifact having one or more pre-determined features characteristic of the pathogen;

If an artifact with the pathogen-specific features is found, performing the following steps:

in a step 360 obtaining the spectrum of the third radiation from a location within the sample corresponding to the image artifact, for example by performing a CARS frequency scan as described hereinabove, or utilizing broadband multiplexed CARS; in a step 370 comparing one of the spectrum of the third radiation, i.e. the CARS spectrum, or a corresponding Raman spectrum obtained therefrom with a saved reference spectrum; if a match is detected, in a step 380 generating a pathogen report or an alarm.

The steps 330-380 are repeated for a next test sample or a next location in the test sample, as schematically shown by a block 390.

The apparatus and methods described herein can be used in water treatment facilities, centralized water testing facilities for testing water samples from various locations and water reservoirs, and the likes, to assess occurrence in water or water samples of substantially any water-borne pathogen that exhibits identifiable CARS spectrum and CARS image characteristics. Examples of pathogens that can be detected in water samples using the methods described herein include protozoa such as those of the genus *Cryptosporidium* and the genus *Giardia*; bacteria such as *Escherichia coli, Yersinia pestis, Francisella tularensis, Brucella* species, *Clostridium perfringens, Burkholderia mallei, Burkholderia pseudomallei, Chlamydia psittaci, Coxiella burnetii, Rickettsia prowazekii, Vibrio* species; *Enterococcus faecalis; Staphylococcus epidermidis; Staphylococcus aureus; Enterobacter aerogenes; Corynebacterium diphtheriae; Pseudomonas aeruginosa; Acinetobacter calcoaceticus; Klebsiella pneumoniae; Serratia marcescens*; yeasts such as *Candida albicans*; and viruses, including filoviruses such as Ebola and Marburg viruses, naviruses such as Lassa fever and Machupo viruses, alphaviruses such as Venezuelan equine encephalitis, eastern equine encephalitis, and western equine encephalitis, rotoviruses, calciviruses such as Norwalk virus, and hepatitis (A, B, and C) viruses, and biological warfare agents such as smallpox (i.e., variola major virus). The methods described herein can be used to distinguish between viable and non-viable forms of these organisms and between infectious and non-infectious forms.

Although the invention has been described hereinabove with reference to particular embodiments thereof, it should be understood that theses embodiments are examples only and should not be construed as limiting the invention. It should also be understood that each of the preceding embodiments of the present invention may utilize a portion of another embodiment.

Of course numerous other embodiments may be envisioned without departing from the spirit and scope of the invention.

We claim:

1. A method of assessing the presence of a pathogen in a sample comprising the steps of:
   a) irradiating the sample with first radiation having a spectrum centered at a first frequency and second radiation having a spectrum including a second frequency, wherein the first frequency exceeds the second frequency by a pre-determined non-zero frequency shift characteristic to the pathogen;
   b) detecting third radiation scattered from or transmitted through the sample at a third frequency that is different from the first and second frequencies, so as to form an image of at least a portion of the sample; and,
   c) analyzing the image to assess occurrence of one or more image artifacts each having one or more pre-determined features characteristic of the pathogen.

2. A method according to claim 1, wherein the third radiation results from a coherent anti-Stokes Raman scattering (CARS) of the first and second radiation within the pathogen, so that the third frequency exceeds the first frequency by an anti-Stokes frequency shift equal to the pre-determined non-zero frequency shift and corresponds to a molecular vibration frequency in the pathogen.

3. A method according to claim 2, wherein the pathogen is *cryptosporidium* oocyst, and the CARS frequency shift is between 500 to 3250 $cm^{-1}$.

4. A method according to claim 3, wherein the CARS frequency shift is equal to one of: $2840+\backslash-60\ cm^{-1}$, $2950+\backslash-50\ cm^{-1}$, and $1650+\backslash-50\ cm-1$.

5. A method according to claim 1, wherein the sample is aqueous fluid.

6. A method according to claim 1, wherein the one or more pre-determined features comprise at least one of shape, pattern and size.

7. A method according to claim 1, wherein step (c) is performed using an image recognition algorithm.

8. A method according to claim 1, further comprising the step of obtaining a spectrum of the third radiation if the presence of an image artifact having one or more pre-determined features characteristic for the pathogen is detected in step (c).

9. A method according to claim 8, wherein the step of obtaining a spectrum of the third radiation comprises the step of varying at least one of the first and second frequencies.

10. A method according to claim 8, wherein the second radiation comprises a plurality of frequencies and is wider in spectrum than the first radiation, and wherein the step of obtaining a spectrum of the third radiation comprises obtaining an instantaneous spectrum of the third radiation using a spectrometer.

11. A method according to claim 8, wherein the spectrum of the third radiation is used to identify the pathogen by comparing said spectrum to one or more stored spectra.

12. A method according to claim 8, wherein the step of varying at least one of the first and second frequencies follows a detection in step (c) of an occurrence of the image artifact having features characteristic to the pathogen.

13. A method of real-time water monitoring for the presence of a pathogen in water, comprising the steps of:
   flowing the water through a trap medium for accumulating the pathogen in a sample carried by the trap medium; and,
   assessing the presence of the pathogen in the sample carried by the trap medium by using the method of claim 2.

14. A method of claim 13, wherein the trap medium is moving through the flowing water at a pre-determined rate, and wherein steps (a) to (c) of the method of claim 2 are performed repeatedly to provide real-time estimates of the presence and concentration of the pathogen in the water.

15. A method of claim 13, wherein the trap medium is in the form of a slurry.

16. A method of claim 13, wherein the trap medium is a microporous filter adapted for trapping the pathogen.

17. A system for real-time monitoring of the presence of a pathogen in water, comprising:
   a trap medium;
   water directing means for directing the water through the trap medium for trapping the pathogen in the trap medium for forming a sample;
   means for moving the trap medium carrying the sample out of the water;
   a CARS optical source for generating a pump beam at a pump optical frequency and a Stokes beam at a Stokes optical frequency;
   a CARS imaging system, comprising:
      optical means for directing the pump and Stokes beams coaxially onto a portion of the trap medium comprising the sample, and
      an optical detector for detecting light from the aqueous sample at a frequency that is shifted from the pump optical frequency by a CARS frequency shift for forming an image of a portion of the sample;
   a processor programmed for analyzing the image to assess occurrence of one or more image artifacts having a shape, size or intensity pattern that is characteristic to the pathogen.

18. A system according to claim 17, wherein the CARS optical source comprises a first laser for generating the pump beam, and a second laser for generating the Stokes beam.

19. A system according to claim 17, wherein the CARS optical source comprises
   an optical pulse source for generating picosecond or sub-picosecond optical pulses; and,
   means for forming the pump and Stokes beams from said picosecond or sub-picosecond optical pulses.

20. A system according to claim 19, wherein the means for forming the pump and Stokes beams comprise:
   a nonlinear dispersive optical element followed by an optical filter for forming the Stokes beam;
   a chirp inducing element for inducing a negative chirp in an incident light pulse, followed by a dispersive element for generating the pump beam; and,
   a beam splitter for splitting light from the optical pulse source into first and second portions, and for directing said first and second portions to the nonlinear dispersive optical and the chirp inducing element, respectively.

21. A method of claim 1, further comprising the step of automatically generating an alert once the presence of one or more pathogens is detected.

22. A system according to claim 17, wherein the processor is programmed for estimating a pathogen concentration in the water.

23. A system according to claim 17, wherein the CARS imaging system further comprises a microlens array means for focusing the pump and Stokes beams into a plurality of focal locations in the sample, and a photodetector array for detecting optical radiation generated at each of the plurality of focal locations.

24. A system according to claim 23, wherein the microlens array means comprises a spinning micro-lens array disk for raster scanning the sample for forming the image.

* * * * *